US007977460B2

(12) United States Patent
Barrowcliffe

(10) Patent No.: US 7,977,460 B2
(45) Date of Patent: Jul. 12, 2011

(54) COMPOSITIONS COMPRISING COAGULATION FACTORS IXA AND VIII FOR THE TREATMENT OF HAEMOPHILIA A OR B

(75) Inventor: Trevor Barrowcliffe, Potters Bar (GB)

(73) Assignee: National Institute for Biological Standards and Control, Hertfordshire (GB)

( * ) Notice: Subject to any disclaimer, the term of this patent is extended or adjusted under 35 U.S.C. 154(b) by 0 days.

(21) Appl. No.: 10/829,042

(22) Filed: Apr. 21, 2004

(65) Prior Publication Data

US 2004/0235737 A1    Nov. 25, 2004

(30) Foreign Application Priority Data

May 19, 2003 (GB) .................................. 0311465.9
Aug. 8, 2003 (GB) .................................. 0318533.7

(51) Int. Cl.
*A61K 38/39* (2006.01)
(52) U.S. Cl. ........ 530/381; 530/380; 530/350; 530/300; 514/2; 514/12
(58) Field of Classification Search .................. 530/383, 530/350, 330; 514/12, 2
See application file for complete search history.

(56) References Cited

U.S. PATENT DOCUMENTS

| 4,348,384 A * | 9/1982 | Horikoshi et al. ............ 424/450 |
| 4,459,288 A | 7/1984 | Thomas |
| 4,501,731 A | 2/1985 | Tishkoff et al. |
| 4,965,199 A * | 10/1990 | Capon et al. ................. 435/69.6 |
| 4,994,371 A | 2/1991 | Davie et al. |
| 5,506,112 A * | 4/1996 | Lang et al. ...................... 435/13 |
| 5,839,443 A * | 11/1998 | Rose et al. ..................... 128/898 |
| 5,925,739 A * | 7/1999 | Spira et al. .................... 530/383 |
| 5,972,885 A * | 10/1999 | Spira et al. ..................... 514/12 |
| 6,013,620 A | 1/2000 | Turecek et al. |
| 2003/0203845 A1* | 10/2003 | Knudsen et al. ................ 514/12 |

FOREIGN PATENT DOCUMENTS

| GB | 2 125 409 | 3/1984 |
| WO | WO 88/00210 | 1/1988 |
| WO | WO 01/27079 | 4/2001 |

OTHER PUBLICATIONS

Elodi et al., Optimization and conditions for the catalytic effect of the factor IXa-factor VIII complex, Thrombosis Research 15, p. 617-629, (1979).*
Barry et al., Proteolytic interactions of factor IXa with human factor VIII and factor VIIIa, Blood, vol. 80, No. 12 (Dec. 15, 1992).*
T. W. Barrowcliffe, et al., Binding To Phospholipid Protects Factor VIII From Inactivation By Human Antibodies. J. Lab. Clin. Med., Jan. 1983, vol. 101, No. 1, p. 34-43.
Karin Fijnvandraat, et al., A Human Alloantibody Interferes With Binding Of Factor IXa To The Factor VIII Light Chain, Blood, Apr. 1, 1998, vol. 91, No. 7, p. 2347-2352.
Abstract 2028: Eva H. N. Olsen, et al., Cross-Linking Of Three Factor VIII Peptides To Factor IXa: Support For Multiple Domain Interactions Between Factor IXa And Its Cofactor. Poster Board # Session: 257-III.
L. M. Aledort, Is The Incidence And Prevalence Of Inhibitors Greater With Recombinant Products? Yes, Journal Of Thrombosis and Haemostasis ((2004) vol. 2, p. 861-862.
R. G. Di Scipio, et al., Activation Of Human Factor IX (Christmas Factor), J. Clin. Inves. (1978) vol. 61, No. 6, p. 1528-1538.
David Gailani, Activation Of Factor IX By Factor XIa, TCM (2000) vol. 10, No. 5, p. 198-204.
I. Hvid, et al., Orthopaedic Surgery In Haemophilic Patients With Inhibitors: An Overview, Haemophilia (2002) vol. 8, p. 288-291.
Barry J. Lamphear, et al., Proteolytic Interactions Of Factor IXa With Human Factor VIII And Factor VIIIa, Blood (1992) vol. 80, No. 12, p. 3120-3126.
J.H. McIntosh, et al., A Modified Thrombin Generation Test For The Measurement Of Factor VIII Concentrates, Journal of Thrombosis and Haemostasis, vol. 1, p. 1-7.
J. Wright, et al., The Epidemiology Of Inhibitors In Haemophilia A: A systematic Review, Haemophilia (2003) vol. 9, p. 418-435.
Abstract: M. Shima, et al., The Current Situation And Vision Of Plasma Protein Formulation . . . , Biomedical Perspectives (1999) vol. 8, No. 1, p. 99-107.
Abstract: A. Yoshioka, Recombinant Factor VIII, 8. Recombinant Factor VIII Formuation, Jap. J. Transfus. Med. (1992) vol. 38, No. 6, p. 845-849.
Abstract: M. Arai, The Current Situation And Vision Of Plasma Protein . . . ; Biomed. Perspect. (1999) vol. 9, No. 1, p. 108-117.

* cited by examiner

*Primary Examiner* — Hope A Robinson
(74) *Attorney, Agent, or Firm* — Vedder Price P.C.; Thomas J. Kowalski; Deborah L. Lu

(57) ABSTRACT

The present invention relates to the use of FIXa and FVIII in the preparation of a composition for the treatment of haemophilia A or haemophilia B in a subject which does not present with anti-FVIII antibodies. The present invention further relates to a composition comprising FIXa and a composition comprising FVIII for simultaneous, simultaneous separate or sequential use in the treatment of haemophilia A or haemophilia B in a subject which does not present with anti-FVIII antibodies.

4 Claims, 3 Drawing Sheets

COMPOSITIONS COMPRISING COAGULATION FACTORS IXA AND VIII FOR THE TREATMENT OF HAEMOPHILIA A OR B

REFERENCE TO RELATED APPLICATIONS

This application claims priority to United Kingdom Patent Applications 0311465.9 filed May 19, 2003 and 0318533.7 filed Aug. 7, 2003. Each of these applications, and each application and patent mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

It is noted that in this disclosure, terms such as "comprises", "comprised", "comprising", "contains", "containing" and the like can have the meaning attributed to them in U.S. patent law; e.g., they can mean "includes", "included", "including" and the like. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. patent law; namely, that these terms are closed ended.

FIELD OF INVENTION

The present invention relates to compositions for the treatment of haemophilia.

In particular, the present invention relates to the use of a composition comprising FIXa and FVIII in the preparation of a composition for the treatment of haemophilia A or haemophilia B in a subject.

BACKGROUND TO THE INVENTION

The process of blood coagulation involves a series of proteins known as blood coagulation proteins which act in a cascade fashion to effect the formation of a blood clot.

The molecular mechanism of blood coagulation and the components that are involved in this are comprehensively described in several review articles (Furie, B. and Furie, B. C., Cell 53 (1988) 505-518; Davie, E. W. et al., Biochem. 30 (1991) 10363-10379; Bergmeyer, H. U. (ed.): Methods of Enzymatic Analysis, Vol. V, chapter 3, 3rd ed., Academic Press, New York (1983)).

Haemophilia is a disease of humans and other mammals wherein a gene encoding a blood coagulation factor contains a mutation such that the encoded protein does not function normally in the cascade process.

Haemophilia A is the most common form of the disorder and is an X-linked, recessive, bleeding disorder caused by a deficiency in the activity of coagulation Factor VIII. Affected individuals develop a variable phenotype of haemorrhage into joints and muscles, easy bruising, and prolonged bleeding from wounds. The disorder is caused by heterogeneous mutations in the Factor VIII gene which maps to Xq28. Despite the heterogeneity in Factor VIII mutations, carrier detection and prenatal diagnosis can be done by direct detection of selected mutations (especially the inversions), as well as indirectly by linkage analysis. Replacement of Factor VIII is done using a variety of preparations derived from human plasma or recombinant techniques. While replacement therapy is effective in most cases, 10 to 25% of treated individuals develop neutralising antibodies that decrease its effectiveness. The mainstay of routine treatment for haemophilia A is infusion of Factor VIII done using amounts that are required to restore the Factor VIII activity to therapeutic levels. Since the half-life of Factor VIII is 11-16 hours twice daily infusions may be required in some circumstances.

The hereditary disease, haemophilia B, is characterised by a mutation in the gene encoding the blood coagulation protein, Factor IX. Factor IX is reviewed in High et al. (1995, "Factor IX" In: Molecular Basis of Thrombosis and Hemostasis, High and Roberts, eds., Marcel Dekker, Inc.).

In 1936, Patek and Stetson (J. Clin. Invest. 15, 531-542) reported that haemophilia could be corrected by the replacement of Factor VIII. Unfortunately, about 15% of haemophilia patients develop antibodies to Factor VIII (Roberts (1981) N. Engl. J. Med. 305, 757), which poses a major difficulty for treatment of these patients.

As reported in Barrowcliffe et al. (1983) J. Lab. Clin. Med., one form of treatment for this group of patients that has been reported is FEIBA (Baxter Healthcare Corporation, USA). FEIBA is a plasma derived protein complex that is used in patients with Haemophilia A with inhibitors, which overcomes the need for Factor VIII and enables blood clots to form.

Barrowdliffe et al. (1981) Thromb. Res. 21, 181 found that FEIBA contained a form of Factor VIII that contributed 30% to 50% of the overall in vitro clot-promoting activity in inhibitor plasma. The results suggested that the Factor VIII may exist as a complex with Factor IXa and phospholipid and in this form may be partially protected from interaction with inhibitors. Barrowcliffe et al. (1981) also reported that the addition of purified factor IXa and phospholipid could protect factor VIII from subsequent inactivation by antibody and that the major protective effect was provided by the phospholipid.

The present invention seeks to provide improved compositions for the treatment of haemophiliac patients.

SUMMARY OF THE INVENTION

The present invention is based in part upon the surprising finding that FIXa allows the concentration of FVIII in a composition for the treatment of haemophilia A or haemophilia B to be reduced, when compared to a composition which does not comprise FIXa.

Thus, in a first aspect, the present invention relates to the use of FIXa and FVIII in the preparation of a composition for the treatment of haemophilia A or haemophilia B in a subject which does not present with anti-FVIII antibodies.

In a second aspect, the present invention relates to a composition comprising FIXa and a composition comprising FVIII for simultaneous, simultaneous separate or sequential use in the treatment of haemophilia A or haemophilia B in a subject which does not present with anti-FVIII antibodies.

In a third aspect, the present invention relates to the use of FIXa in the manufacture of a composition comprising FVIII for the treatment of haemophilia A or haemophilia B, wherein the presence of FIXa allows the concentration of FVIII in the composition to be reduced in comparison to a composition which does not comprise FIXa.

In a fourth aspect, the present invention relates to a method for treating a subject suffering from haemophilia A or haemophilia B, comprising administering to a subject in need thereof a composition comprising FIXa and FVIII, wherein said subject does not present with anti-FVIII antibodies.

In a fifth aspect, the present invention relates to a method for treating a subject suffering from haemophilia A or haemophilia B, comprising administering to a subject in need thereof a composition comprising FIXa and FVIII, wherein said composition comprises FVIII in an amount lower than that required for treatment of said subject with a composition lacking FIXa.

In a sixth aspect, the present invention relates to a method for potentiating FVIII comprising the step of mixing together Factor FVIII and FIXa into a composition.

Other aspects of the present invention are presented in the accompanying claims and in the following description and discussion. These aspects are presented under separate section headings. However, it is to be understood that the teachings under each section heading are not necessarily limited to that particular section heading.

Preferably, the composition comprising FIXa further comprises phospholipid.

Preferably, the composition of the present invention further comprises phospholipid.

Preferably, the composition is administered to a subject which does not present with anti-FVIII antibodies.

Preferably, the FVIII and FIXa reagents are produced using recombinant DNA technology.

Moreover it is proposed that the addition of FIXa and phospholipid would reduce the immunogenicity of FVIII, reducing the incidence of anti-FVIII inhibitors in haemophilia patients and/or the rapidity of the onset of such inhibitors. The basis of this supposition is that the phospholipid binding and FIXa binding regions of the FVIII molecule, on the C2 domain and the A2 domain respectively, are immunodominant regions, hence covering these regions by binding to the respective ligands should reduce the antigenic response to these epitopes. Therefore, the invention provides a method for reducing the immunogenicity of FVIII, comprising providing FVIII to a patient in admixture with or simultaneously with FIXa and phospholipid. Likewise, the invention provides the use of FIXa and phospholipid in the preparation of a composition for the reduction of immunogenic reactions to FVIII in the treatment of haemophilia in a subject.

Advantages

The present invention has a number of advantages. These advantages will be apparent in the following description.

By way of example, the present invention is advantageous since it provides a commercially useful composition.

By way of example, the present invention is advantageous since lower amounts of Factor VIII are required in compositions for the treatment of haemophilia A or haemophilia B. Therefore, the compositions of the present invention may be cheaper than existing therapies.

By way of further example, the present invention is advantageous because it provides an additional therapy for the treatment of haemophilia A or haemophilia B.

By way of further example, the present invention is advantageous because it provides an additional therapy for the treatment of haemophilia A or haemophilia B in subjects that present with anti-FVIII antibodies.

Furthermore, the invention prevents and/or retards the occurrence of anti-FVIII antibodies in haemophilia patients by reducing the immunogenenicity of natural or recombinant FVIII during the therapy. It is believed that FIXa masks the antigenic epitopes of FVIII, rendering it less immunogenic in the circulation.

Figure 1:
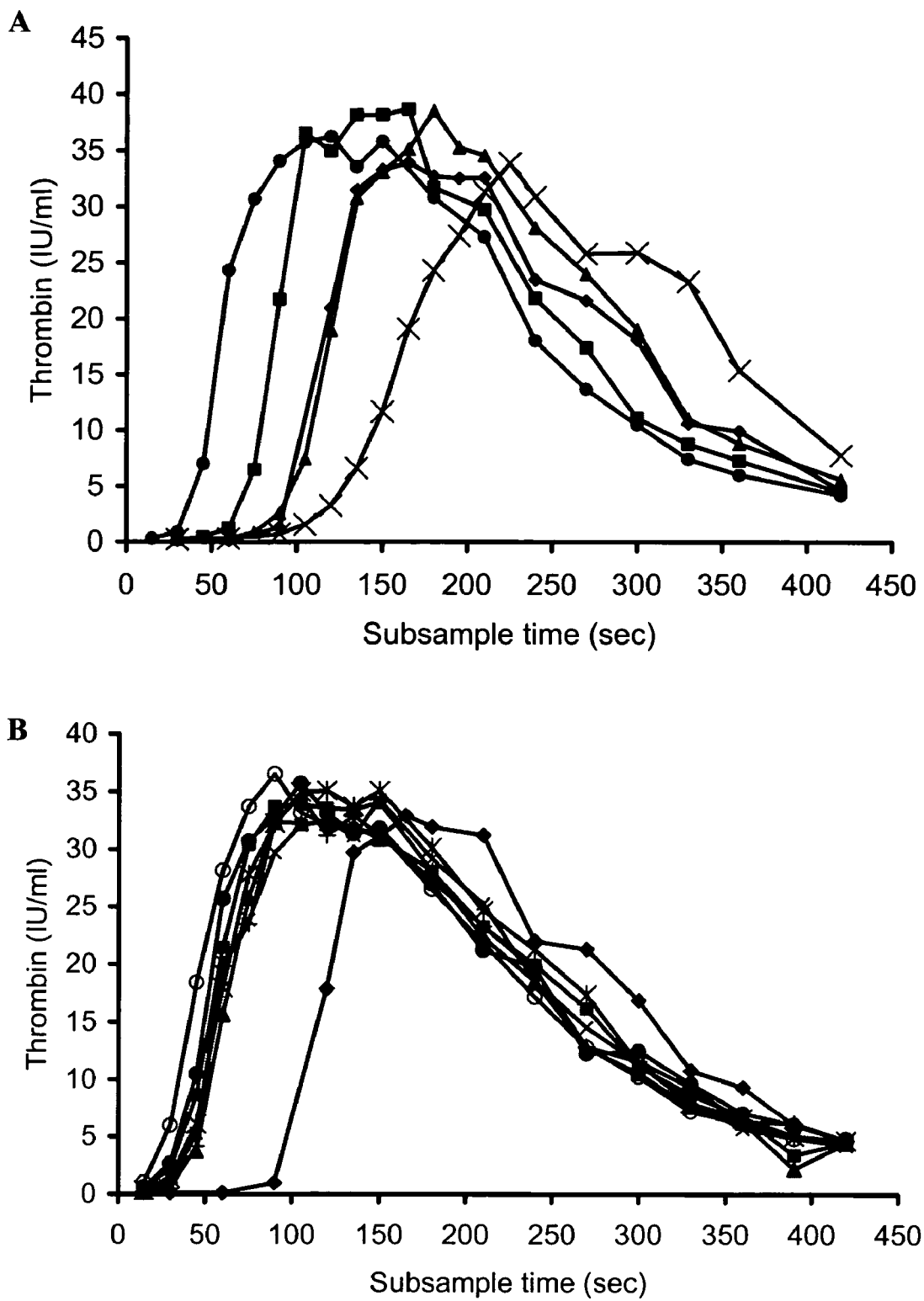
FIG. 1

Thrombin generation by FVIII concentrates with high FIXa (14 nM). A. Dose-Response of a FVIII concentrate. Concentrate HP(Mo-Ab)2 was diluted into artificial FVIII deficient plasma at concentrations of 1 (¶), 0.125 (■), 0.03(σ) and 0.005 IU/ml (x). Normal plasma (♦). B. Comparison of thrombin generation by different FVIII concentrates. FVIII concentrates were added at 1 IU/ml to artificial FVIII deficient plasma. rFVIII BDD (○), rFVIII FL1 (■), rFVIII FL2 (σ), HP(Mo-Ab) 1 (x), HP (Mo-Ab) 2 (*), HP (Ion-ex) (λ), IP (+), Normal plasma (υ).

FIG. 2

Thrombin generation profile by different FVIII deficient plasmas. All deficient plasmas were <0.01 IU/ml. Normal plasma (υ), two severe haemophilic plasmas from patients four days post-transfusion 1 (-*-), 2(--*--), commercial haemophilic plasma (+), artificially depleted plasma (○).

FIG. 3

Effect of FIXa on thrombin generation A. Effect of FIXa concentration on thrombin generation. Two different FIXa concentrations were used to activate thrombin generation. FIXa concentration of 14 nM solid line, or 0.2 nM dashed line was added to initiate coagulation. Normal plasma (υ), haemophilic plasma (*). B dose-response of FVIII concentrate at low FIXa concentration. HP(Mo-Ab)2 was diluted into haemophilic plasma of patient 1. Thrombin generation was triggered with FIXa concentration of 0.2 nM. Normal plasma (υ), 1 (λ), 0.125 (v), 0.03 IU/ml (σ), and haemophilic plasma (*).

DETAILED DESCRIPTION OF THE INVENTION

Haemophilia

Haemophilia is a group of hereditary bleeding disorders of specific blood clotting factors classified as haemophilia A and B.

As described herein, the present invention relates to the treatment of haemophilia A and B. In a highly preferred embodiment, the present invention relates to the treatment of haemophilia A.

Haemophilia A

General teachings on haemophilia A can be found in Semin Thromb Hemost (2002) 28(3):309-22; Mol Pathol (2002) 55(2), 127-44; Baillieres Clin Haematol (1996) 9(2):211-28; Hum Mutat (1995) 5(1):1-22; and Adv Hum Genet (1988) 17:27-59; and O'Brien D P, Tuddenham E G D, The structure and function of factor VIII. In: "Haemostasis & thrombosis", Ed Bloom A, Forbes C D, Thomas D P, Tuddenham E G D, Churchill Livingstone, 1993, 333-348.

Background teachings on haemophilia A have been presented by Victor A. McKusick et al on http://www.ncbi.nlm-.nih.gov/Omim. The following information concerning haemophilia has been selected and extracted from that source:

Haemophilia A is an X-linked, recessive, bleeding disorder caused by a deficiency in the activity of coagulation factor VIII. Affected individuals develop a variable phenotype of haemorrhage into joints and muscles, easy bruising, and prolonged bleeding from wounds. The disorder is caused by heterogeneous mutations in the factor VIII gene which maps to Xq28. Despite the heterogeneity in factor VIII mutations, carrier detection and prenatal diagnosis can be done by direct detection of selected mutations (especially the inversions), as well as indirectly by linkage analysis. Replacement of factor VIII is done using a variety of preparations derived from human plasma or recombinant techniques. While replacement therapy is effective in most cases, 10 to 15% of treated individuals develop neutralising antibodies that decrease its effectiveness.

Affected individuals develop a variable phenotype of haemorrhage into joints and muscles, easy bruising, and prolonged bleeding from wounds. Haemophilia A and B are clinically similar and can only be distinguished by assays of factor VIII and IX activity. In contrast von Willebrand disease more often presents with mucocutaneous or gastrointestinal haemorrhage or menorrhagia. Tests used in its diagnosis include bleeding time, platelet aggregation, and factor VIII and von Willebrand factor assays.

The severity and frequency of bleeding in haemophilia A is inversely related to the amount of residual factor VIII (<1%, severe; 2-5%, moderate; and 5-30%, mild).

Haemophilia A is the result of a hereditary defect in antihemophilic globulin (factor VIII). Factor VIII has a molecular weight of 330,000 and circulates in plasma at a concentration of 100 ng/mL, bound noncovalently to von Willebrand Factor (VWF), which acts as a stabiliser and carrier protein. It is synthesised primarily in the liver. VWF circulates in plasma at a concentration of 5-10 µg/mL and has a M Wt of 250,000 as a monomer, but circulates as a series of multimers with molecular weights up to 20 million. Factor VIII is encoded by the factor VIII gene on Xq28 while the vWF which affects bleeding time and ristocetin aggregation of platelets is encoded by a gene on chromosome 12.

The mainstay of routine treatment for haemophilia A is infusion of factor VIII done using amounts that are required to restore the factor VIII activity to therapeutic levels. Since the half-life of factor VIII is 11 -16 hours twice daily infusions may be required in some circumstances.

Haemophilia B

General teachings on haemophilia B can be found in Mol Pathol (2002) 55(2), 127-44; Baillieres Clin Haematol. (1996) 9(2):211-28; Adv Hum Genet (1988) 17:27-59; and Haemophilia (1998) 4(4):350-7.

Haemophilia B is characterised by a deficiency in factor IX, which results in prolonged bleeding after injuries and surgery etc, renewed bleeding after initial bleeding has stopped, and delayed bleeding. In severe haemophilia B, spontaneous joint bleeding is the most frequent symptom.

The age of diagnosis and frequency of bleeding episodes are related to the factor IX clotting activity. Patients with severe haemophilia B are usually diagnosed during the first year of life. Without treatment, they have an average of two to five spontaneous bleeding episodes each month. Patients with moderately severe haemophilia B seldom have spontaneous bleeding; however, they do have prolonged or delayed bleeding after relatively minor trauma and are usually diagnosed before the age of five to six years. The frequency of bleeding episodes varies from once a month to once a year. Patients with mild haemophilia B do not have spontaneous bleeding; however, without treatment, abnormal bleeding occurs with surgery, tooth extraction, and major injuries. The frequency of bleeding may vary from once a year to once every ten years. Patients with mild haemophilia B are often not diagnosed until later in life. In any patient, bleeding episodes may be more frequent in childhood and adolescence than in adulthood.

The diagnosis of haemophilia B is established in individuals with low factor IX clotting activity. Molecular genetic testing of the factor IX gene (chromosomal locus Xq27.1-q27.2) identifies disease-causing mutations in over 99% of patients with haemophilia B.

Factor IXa

As used herein, the term "factor IXa" relates to any functional factor IXa protein of fragment thereof including any recombinant, hybrid or modified form of factor Ixa.

The hybrid or modified form of factor IXa includes any functional factor IXa protein or fragment thereof which comprises factor IXa amino acid sequences—such as factor Ixa amino acid sequences from mammals (eg. humans and animals).

Factor IXa (FIXa) is produced from its inactive precursor, factor IX, via proteolytic cleavage by factor XIa or the tissue factor/factor VIIa/phospholipid complex. The activation results from the cleavage of two peptide bonds in the factor IX molecule, releasing an activation glycopeptide with an apparent molecular weight of 10,000. The heavy chain of factor Ixa (Mr=28,000) contains the serine protease catalytic domain, while the light chain (Mr=17,000) contains the membrane binding domain.

The activation of factor IX by factor IXa is reviewed in *Trends Cardiovasc Med* (2000) 10(5), 198-204

Factor IXa functions as a serine protease involved in the activation of the zymogen, factor X, to form the enzyme, factor Xa.

The Factor IXa according to the present invention may also be a modified form of naturally occurring Factor IXa—such as chemically modified form. The Factor, IXa may be any recombinant form of Factor IXa—such as a mutant form of Factor IXa. If a modified form of Factor IXa is used then generally the modified form will have advantageous properties in comparison to the naturally occurring form. Such properties may include enhanced stability, enhanced activity, ease of preparation or a reduced cost of preparation for example.

Factor IXa may be prepared using various methods that are known in the art. By way of example, factor IXa may be prepared from highly purified factor IX by activation with factor XIa. The factor IXa may be further purified by gel filtration, followed by immunoaffinity purification. Purity may be assessed by SDS-PAGE analysis. Activity may be determined in a one-stage clotting assay as described by Over (1984) Scandinavian Journal of Haematology Supplementum No. 41, 33 13-24.

Advantageously, the Factor IXa that is used is prepared by recombinant DNA techniques.

Recombinant FIXa (97/562) may be obtained from NIBSC (Potters Bar, UK).

Preferably, the recombinant FIXa is substantially purified—such as 99% purified.

The FIXa reagent may be checked for the absence of FVIII and tissue factor in a factor Xa generating system (Barrowcliffe et al. (2002) Thromb. Haemost 87, 442-9.

Nucleotide and amino acid sequences for Factor IXa are available in databases.

Factor VIII

As used herein, the term "factor VIII" relates to any functional factor VIII protein molecule including any hybrid factor VIII or modified factor VIII.

The hybrid or modified factor VIII may include any functional factor VIII protein molecule or fragment thereof which comprises factor VIII amino acid sequences from mammals—such as humans and animals.

Human factor VIII is a trace plasma glycoprotein involved as a cofactor in the activation of factor X and factor IXa. Inherited deficiency of factor VIII results in the X-linked bleeding disorder haemophilia A which can be treated successfully with purified factor VIII. The replacement therapy of haemophilia A has evolved from the use of plasma-derived factor VIII to the use of recombinant factor VIII obtained by cloning and expressing the factor VIII cDNA in mammalian cells. (Wood et al., 1984, Nature 312: 330).

Factor VIII has a domain organisation of A1-A2-B-A3-C1-C2 and is synthesised as a single chain polypeptide of 2351 amino acids, from which a 19-amino acid signal peptide is cleaved upon translocation into the lumen of the endoplasmic reticulum.

Factor VIII may be in the form of a plasma fraction which also contains other protein materials—such as fibrinogen and fibronectin. Such a Factor VIII preparation can readily be prepared by any of the isolation techniques known in the art (see, for example, "Human Blood Coagulation, Haemostasis and Thrombosis", Ed. R. Biggs, $2^{nd}$ Edition (1976), Blackwell Scientific Publications, Chapter 11).

A freeze dried intermediate purity preparation of Factor VIII may be used as described by Newman et al. (1971) British Journal of Haematology 21, 1.

The Factor VIII may be subjected to treatment by heat, solvent, detergent or other techniques in order to inactivate viruses.

Efforts have been made in recent years to manufacture Factor VIII from recombinant sources to avoid potential contamination associated with blood products. In addition, a recombinant source for Factor VIII provides a virtually unlimited supply of the coagulation factor, thus avoiding supply limitations associated with using donated blood plasma as a source material.

Advantageously, the Factor VIII that is used is therefore prepared by recombinant DNA techniques.

Human factor VIII cDNA may be obtained by isolating it from an appropriate genomic source (i.e., human liver which is the natural organ for production of this protein) by various methods which include preparation of cDNAs from isolated mRNA templates, direct synthesis, or some combination thereof, as described in U.S. Pat. No. 4,757,006.

Host-vector systems for the expression of Factor VIII may be prokaryotic, but the complexity of Factor VIII makes the preferred expression system (at least for biologically-active Factor VIII having clotting activity) a mammalian one. This may be accomplished by eukaryotic (usually mammalian or vertebrate cells) transformation with a suitable Factor VIII vector.

An expression system for Factor VIII is described in U.S. Pat. No. 6,358,703. The expression of factor VIII in recombinant and transgenic systems is reviewed in Blood Cells Mol Dis (2002) 28(2), 234-48.

The cDNAs encoding factor VIII or individual fragments or modified proteins thereof may be fused, in proper reading frame, with appropriate regulatory signals to produce a genetic construct that is then amplified, for example, by preparation in a bacterial (e.g., E. coli) plasmid vector, according to conventional methods—such as those described in Sambrook et al., Molecular Cloning: A Laboratory Manual (Cold Spring Harbor Press 1989). The amplified construct is then excised from the vector and purified for use. Purification may be accomplished by various methods known in the art—such as by means of one or more cycles of HPLC.

The Factor VIII that is used may also be selected from the reference preparations from NIBSC listed in Table 1. rFVIII BDD (99/694) is a recombinant FVIII lacking the B-domain (the B-domain is not thought to have any effect on haemostasis). The full-length recombinants are manufactured by slightly different methods (rFVIII FL1&2, 96/598, 96/590), FL1 is manufactured by insertion of cDNA for FVIII and vWF into the Chinese hamster ovary cell line (Lee (1999) Thromb Haemost 82: 516-524). FL2 is manufactured by the insertion of FVIII cDNA into the baby hamster kidney cell line, both have similar purification steps and require albumin for stabilisation. High purity monoclonal antibody purified (HP (Mo-Ab)1&2, 96/574, 95/640) uses FVIII antibodies which are covalently bound to sepharose beads in a column, the antibodies adsorb FVIII as cryoprecipitate is passed over the column, the FVIII is released from the column with an elution buffer, the material is then further purified (Lee C A. Coagulation factor replacement therapy. In: Recent Advances in Haematology (Hoffbrand A V and Brenner M K, eds), No 6. Edinburgh: Churchill Livingstone. p73-88). High purity ion exchange purified (HP(Ion-ex), 96/600) is manufactured by first chromatographically purifying cryoprecipitate which is then followed by ion-exchange resin to further purify the FVIII by adsorption. Intermediate purity (IP, 96/574) was purified by heparin and glycine precipitation (Kasper Cota e Silva (2000) In: Facts and Figures, No 6. Montreal: World Federation of Hemophilia. 2000; 5-6). Potencies were measured by the chromogenic method against the WHO concentrate standard.

Nucleotide and amino acid sequences for Factor VIII are available in databases.

Phospholipid

Generally, the best source of phospholipid are platelets themselves in the form of platelet-rich plasma obtained from a severe haemophilic (Nilsson et al. (1957) Acta. Med. Scand. 159, 35-57 (1957)). However, this is not a practical approach for the majority of laboratories and other phospholipid sources have to be used.

A mixture of a negatively charged phospholipid—such as phosphatidylserine—and an uncharged phospholipid—such as phosphatidylcholine—may serve as a suitable reagent (Zwaal & Hemker (1982) Haemostasis 11, 12-39).

Phospholipid extracts of different sources may be used—such as bovine, rabbit or human brain, as described in Bell and Alton (1954) Nature 174, 880-881; Hjort et al. (1955) J. Lab. Clin. Med. 46, 89-97; and Barrowdliffe et al. (1982) Haemostasis 11, 96-101).

The phospholipid may be substantially purified or synthetic phospholipid.

The phospholipid may consist of purified or synthetic phospholipid either alone or in admixture with other materials—such as phosphatidyl choline, phosphatidyl ethanolamine, phosphatidyl inositol and sphingomyelin.

The phospholipid may be extracted, using a non-polar solvent, form a human, animal or plant tissue that is rich in phospholipid. Suitable tissue sources may include bovine, human, porcine or rabbit brain, placenta, spinal chord, or platelets, with bovine or human brain being a particularly good source that is rich in phospholipid.

Any non-polar solvent that yields, on extraction of the tissue, phospholipid with the required level of phospholipid may be used in this process. Suitable solvents may include, but are not limited to, chlorinated alkanes—such as chloroform and dichloromethane and petroleum ether.

Whatever the choice of extraction solvent and method of extraction, it is preferred if the phospholipid obtained is a stable product and contains a minimum of oxidation products.

This can be best achieved by incorporating a suitable antioxidant, in particular butylated hydroxyanisole, into the solvent or solvents employed.

Once the phospholipid has been obtained by, for example, mixing purified or synthetic phospholipid or extracting these materials from natural sources, the phospholipid may then be dispersed in an aqueous solution by any of the emulsification methods that are known in the art. By way of example, the phospholipid may be dissolved in methanol or ethanol, and then evaporation of most or all of the solvent followed by addition of the solid to water or physiological saline with vigorous mixing affords a phospholipid emulsion.

In a preferred embodiment, the phospholipid (91/542) is obtained from NIBSC, Potters Bar, UK.

Treatment

It is to be appreciated that all references herein to treatment include one or more of curative, palliative and prophylactic treatments. Preferably, the term treatment includes at least curative treatment and/or palliative treatment.

The treatment may be combined with other treatments for haemophilia.

Therapy

The compositions of the present invention may be used as therapeutic agents—i.e. in therapy applications.

As with the term "treatment", the term "therapy" includes curative effects, alleviation effects, and prophylactic effects.

The therapy may be on humans or animals.

The therapy may be combined with other therapeutic treatments for haemophilia.

Subject

In the context of the present invention, a "subject" refers to any subject that may develop or has haemophilia—such as mammals, for example humans and animals.

Preferably, a subject according to the present invention is a human.

The subject may or may not present with anti-FVIII antibodies.

The presence of anti-FVIII antibodies may be determined using various methods known in the art—such as those methods described in Barrowcliffe et al. (1983) *J. Lab. Clin. Med.* 34-43.

Generally, subjects that present with anti-FVIII antibody levels of less than 10 Bethesda Units/ml may be treated with high doses of Factor VIII. However, there are a number of problems associated with this treatment because not only does it not always work, but it is also expensive. Subjects with anti-FVIII antibody levels higher than 10 Bethesda Units/ml typically require an alternative treatment because treatment with high doses of Factor VIII does not work.

The compositions of the present invention may therefore be administered to subjects with anti-FVIII antibody levels of less than and higher than 10 Bethesda Units/ml.

In a preferred embodiment, the compositions of the present invention are administered to subjects with anti-FVIII antibody levels of higher than 10 Bethesda Units/ml.

Composition

In accordance with the present invention, FVIII and FIXa may be administered as separate pharmaceutical compositions or administered together as a single pharmaceutical composition.

FVIII and FIXa may also be administered simultaneously, simultaneously separately or sequentially.

The composition may further comprise phospholipid.

Preferably, the composition comprising FIXa may further comprise phospholipid.

Typically, the phospholipid is dispersed in an aqueous solution—such as water or saline—to form a dispersion which is then mixed with the factor IXa.

Accordingly, the compositions according to the present invention may comprise a FVIII pharmaceutical composition and a FIXa plus phospholipid pharmaceutical composition. The compositions according to the present invention may further comprise a pharmaceutical composition comprising FVIII, FIXa and phospholipid.

The compositions according to the present invention may consist essentially of a FVIII pharmaceutical composition and a FIXa plus phospholipid pharmaceutical composition. The compositions according to the present invention may further consist essentially of a pharmaceutical composition comprising FVIII, FIXa and phospholipid.

The compositions of the present invention may also contain further non-toxic materials—such as naturally occurring materials. These further materials are generally derived from plasma or phospholipid rich tissue sources. Typical of these materials are fibrinogen and albumin.

In order to prepare the compositions according to the present invention, one or more of the ingredients may be freeze dried.

If the pharmaceutical composition comprises phospholipid then a mixture of factor IXa and phospholipid (together with any other associated materials) may be prepared by freeze drying. In this case, the composition may be prepared by adding the freeze dried mixture to an aqueous solution.

The compositions described herein may be for human or animal usage in human and veterinary medicine and will typically comprise any one or more of a pharmaceutically acceptable diluent, carrier, or excipient: Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent may be selected with regard to the intended route of administration and standard pharmaceutical practice. Pharmaceutical compositions may comprise as—or in addition to—the carrier, excipient or diluent any suitable binder(s), lubricant(s), suspending agent(s), coating agent(s) or solubilising agent(s).

Accordingly, the components of the compositions of the present invention, may also be in admixture with one or more suitable pharmaceutical excipients, diluents or carriers selected with regard to the intended route of administration and standard pharmaceutical practice.

There may be different composition/formulation requirements dependent on the different delivery systems. By way of example, pharmaceutical compositions useful in the present invention may be formulated to be administered parenterally in which the composition is formulated by an injectable form, for delivery, by, for example, an intravenous, intramuscular or subcutaneous route. Alternatively, the formulation may be designed to be administered by a number of routes.

Preservatives, stabilisers, dyes and even flavouring agents may be provided in pharmaceutical compositions. Examples of preservatives include sodium benzoate, sorbic acid and esters of p-hydroxybenzoic acid. Antioxidants and suspending agents may be also used.

Preferably, the pharmaceutically acceptable diluent or carrier is water. However, this may be replaced by other suitable diluents or carriers, for example, a physiological salt solution.

The compositions of the present invention may be administered in the form of tablets, capsules, ovules, elixirs, solutions or suspensions, which may contain flavouring or colouring agents, for immediate-, delayed-, modified-, sustained-, pulsed- or controlled-release applications.

If the pharmaceutical is a tablet, then the tablet may contain excipients—such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders—such as polyvinylpyrrolidone, hydroxypropylmethylcellulose (HPMC), hydroxypropylcellulose (HPC), sucrose, gelatin and acacia. Additionally, lubricating agents—such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The routes for administration (delivery) may include, but are not limited to, one or more of oral (e.g. as a tablet, capsule, or as an ingestable solution), parenteral (e.g. by an injectable form), intramuscular, intravenous, intraventricular, intradermal or subcutaneous.

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. Alternatively, the formulation may be designed to be administered by a number of routes.

The pharmaceutical compositions may be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood.

Dosage

The possible dosages of the components of the compositions of the present invention may be determined by a person skilled in the art. By way of example, the amounts of the components to be used may be optimised using animal studies.

The dosage of Factor VIII is described in the art in International Units (IU). One IU is the amount of factor VIII in I ml of normal plasma, which is about 100 ng.

The actual dose of Factor VIII that is administered to a subject depends on the clinical circumstances of the subject, as will be appreciated by a person skilled in the art.

Typically, the dosage of Factor VIII when administered alone in accordance with the prior art will be in the range of 20-50 IU/kg.

Advantageously, the amount of Factor VIII that is administrated in accordance with the compositions of the present invention, that is in combination with FIXa and optionally phospholipid, may be reduced by up to 2, 4, 6, 8 or 10-fold or more in vitro. Advantageously, therefore, the compositions of the present invention provide a dosage of below 20 IU/kg, preferably between 2 and 10 IU/Kg, and advantageously between 2 and 5 IU/Kg.

In accordance with the present invention, FIXa should be higher in concentration than FVIII in molar terms.

Preferably, FIXa should be at least 10-100 times the concentration of FVIII in molar terms. More preferably, FIXa should be at least 20-90 times the concentration of FVIII in molar terms. More preferably, FIXa should be at least 30-70 times the concentration of FVIII in molar terms. More preferably, FIXa should be at least 40-60 times the concentration of FVIII in molar terms. Most preferably, FIXa should be at least 50 times the concentration of FVIII in molar terms.

In accordance with the present invention, the phospholipid should be higher in concentration than FVIII in molar terms.

Preferably, the phospholipid should be at least 10-1500 times the concentration of FVIII in molar terms. More preferably, the phospholipid should be at least 10-1000 times the concentration of FVIII in molar terms. More preferably, the phospholipid should be at least 10-900 times the concentration of FVIII in molar terms. More preferably, the phospholipid should be at least 10-800 times the concentration of FVIII in molar terms. More preferably, the phospholipid should be at least 10-700 times the concentration of FVIII in molar terms. More preferably, the phospholipid should be at least 10-600 times the concentration of FVIII in molar terms. More preferably, the phospholipid should be at least 10-500 times the concentration of FVIII in molar terms. More preferably, the phospholipid should be at least 10-400 times the concentration of FVIII in molar terms. More preferably, the phospholipid should be at least 100-400 times the concentration of FVIII in molar terms. More preferably, the phospholipid should be at least 200-400 times the concentration of FVIII in molar terms. Most preferably, the phospholipid should be at least 300 times the concentration of FVIII in molar terms.

The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

Formulation

The component(s) of the present invention may be formulated into a pharmaceutical composition, such as by mixing with one or more of a suitable carrier, diluent or excipient, by using techniques that are known in the art.

Nucleotide Sequence

As used herein, the term "nucleotide sequence" is synonymous with the term "polynucleotide".

Aspects of the present invention involve the use of nucleotide sequences, which are available in databases. These nucleotide sequences may be used to express amino acid sequences that may be used as a component of the composition of the present invention.

The nucleotide sequence may be DNA or RNA of genomic or synthetic or recombinant origin. The nucleotide sequence may be double-stranded or single-stranded whether representing the sense or antisense strand or combinations thereof.

The nucleotide sequence may be prepared by use of recombinant DNA techniques (e.g. recombinant DNA).

The nucleotide sequence may be the same as the naturally occurring form, or may be derived therefrom.

Amino Acid Sequence

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "protein".

Aspects of the present invention concern the use of amino acid sequences, which are available in databases. These amino acid sequences may be used in the compositions of the present invention.

The amino acid sequence may be isolated from a suitable source, or it may be made synthetically or it may be prepared by use of recombinant DNA techniques.

Animal Test Models

In vivo models may be used to optimise or design therapies for the treatment of haemophilia A or haemophilia B in a subject.

The animal test model may be a mammal—such as non-human mammal, for example, a rat, hamster, rabbit, guinea pig or mouse.

General Recombinant DNA Methodology Techniques

The present invention employs, unless otherwise indicated, conventional techniques of chemistry, biology, molecular biology, microbiology and recombinant DNA technology, which are within the capabilities of a person of ordinary skill in the art.

Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

The invention will now be further described by way of Examples, which are meant to serve to assist one of ordinary skill in the art in carrying out the invention and are not intended in any way to limit the scope of the invention.

EXAMPLE 1

Materials and Method

Reagents

TBS Buffer 50 mM Tris, 150 mM NaCl, 0.02% $NaN_2$, pH7.4, 1% human serum albumin (Zenalb, BPL, Elstree, UK). Bovine fibrinogen (Diagnostic Reagents Ltd. Thame, Oxon UK). Lyophilised reagents from NIBSC, Potters Bar, Herts, UK: Phospholipid (91/542), recombinant FIXa (97/562), Ancrod (74/581), α-thrombin (89/588). The FIxa reagent is 99% pure and was checked for the absence of FVIII and tissue factor in a factor Xa generating system (Barrowcliffe T W, Fabregas P, Jardi M, Cancelas J, Rabaneda M, and Feize J. Procoagulant activity of T lymphoblastoid cell due to exposure of negatively charged phospholipid. Thromb Haemost 2002; 87: 442-449).

FVIII Concentrates

A range of concentrates with different purities and manufacturing processes were studied. FVIII concentrates (Table 1) used were lyophilised material which were reference preparations, again from NIBSC. rFVIII BDD (99/694) is a recombinant FVIII lacking the B-domain (the B-domain is not thought to have any effect on haemostasis (Lee C. Recombinant clotting factors in the treatment of hemophilia. Thromb Haemost 1999; 82: 516-524)). The full-length recombinants are manufactured by slightly different methods (rFVIII FL1&2, 96/598, 96/590), FL1 is manufactured by insertion of cDNA for FVIII and vWF into the Chinese hamster ovary cell line (Lee C. Recombinant clotting factors in the treatment of hemophilia. Thromb Haemost 1999; 82: 516-524). FL2 is manufactured by the insertion of FVIII cDNA into the baby hamster kidney cell line, both have similar purification steps and require albumin for stabilisation. High purity monoclonal antibody purified (HP (Mo-Ab)1&2, 96/574, 95/640) uses FVIII antibodies which are covalently bound to sepharose beads in a column, the antibodies adsorb FVIII as cryoprecipitate is passed over the column, the FVIII is released from the column with an elution buffer, the material is then further purified (Lee C A. Coagulation factor replacement therapy. In: Recent Advances in Haematology (Hoffbrand A V and Brenner M K, eds), No 6. Edinburgh: Churchill Livingstone. 1992; 73-88). High purity ion exchange purified (HP(Ion-ex), 96/600) is manufactured by first chromatographically purifying cryoprecipitate which is then followed by ion-exchange resin to further purify the FVIII by adsorption Lee C A. Coagulation factor replacement therapy. In: Recent Advances in Haematology (Hoffbrand A V and Brenner M K, eds), No 6. Edinburgh: Churchill Livingstone. 1992; 73-88). Intermediate purity (IP, 96/574) was purified by heparin and glycine precipitation (Kasper C K and Cota e Silva M. Registry of clotting factor concentrates $2^{nd}$ edn. In: Facts and Figures, No 6. Montreal: World Federation of Hemophilia. 2000; 5-6). Potencies were measured by the chromogenic method against the WHO concentrate standard.

Plasmas

Artificial FVIII deficient plasma (Organon Teknika Corporation, Durham, USA). This plasma was chemically depleted and contains normal vWF levels. Normal platelet free plasma was obtained from the National Blood Service, Colindale, UK. Five donations were pooled together before freezing; the resulting pool contained 0.86 IU/ml FVIII as measured by chromogenic assay. Haemophilic plasma was obtained from 2 patients with levels of less than 0.01 IU/ml as measured by one stage APTT assay. Plasma was spun to remove platelets at 2000 g, 4° C., 15 mins.

Rabbit polyclonal FVIII antibody was a kind gift of Dr Ingerslev. Control antibody was Gammabulin, Baxter Hyland Immuno (Immuno Ltd, Thetford, Norfolk, UK).

The thrombin generation tests were performed on Deca machines (Grifols, Barcelona, Spain), which detected clotting by a mechanical end point.

Thrombin Generation Test

Plasma was defibrinated using ancrod as previously described (Houbouyan L, Padilla A, Gray E, Longstaff C, and Barrowcliffe T W. Inhibition of thrombin generation by heparin and LMW heparins: a comparison of chromogenic and clotting methods. Blood Coagul Fibrinolysis 1996; 7: 24-30), final concentration 0.5 IU per ml of plasma, 37° C. for 30 mins, the clot was then wound out on a wooden stick. FVIII concentrates were added to FVIII deficient plasma to achieve concentrations of 0.005-1 IU/ml. 400 µl normal plasma or deficient plasma and FVIII concentrate and 80 µl FIXa (concentration in plasma 14 nM) were incubated together for 1.5 mins at 37° C., then 400 µl phospholipid (final concentration 3.1 µg/ml) and 400 µl $CaCl_2$ (final concentration 7.8 mM) were added to start the reaction. At frequent intervals 50 µl subsamples were added to 200 µl fibrinogen in cups on two Deca machines which recorded clotting times. The clotting times were then converted into thrombin units by use of an α-thrombin standard curve. The thrombin generation curves were quantitated as area under the curve (AUC), peak thrombin and the time taken to reach half maximal ($T_{1/2max}$). Each experiment was carried out in duplicate in a reverse balanced order, and repeated on three or more separate occasions.

Reproducibility of TGT

Over a 3 month period normal plasma was assayed on 9 separate occasions in duplicate, the 3 parameters of the curves gave a CV range of 8.9-14.6%. In addition a set of 5 repeat experiments was carried out over a week at 3 different FVIII concentrations. CV ranged from 5-5.6% at 0.02 IU/ml, 9.2-11.7% at 0.005 IU/m and 6.8-12.3% for normal plasma (0.86 IU/ml).

FVIII Antibody Experiments

Antibodies were added to normal and haemophilic plasma at a dilution of 1 in 1000 for the FVIII antibody and at 10 µg/ml for the control antibody. The plasmas and antibodies were incubated overnight at 37° C., the thrombin generation test was then carried out as before.

Data Analysis

Statistical analysis was determined using the unpaired students t-test.

EXAMPLE 2

Dose-Response of TGT to FVIII

Concentrate HP(Mo-Ab)2 was spiked into artificial chemically depleted FVIII deficient plasma over a wide range of FVIII concentrations from 0.005 to 1 IU/ml and the thrombin generation measured (FIG. 1A). It was found that as the concentration of FVM decreased from 1 to 0.005 IU/ml the lag time of the curves as represented by the $T_{1/2max}$ lengthened from 64 to 165 seconds. However, despite a very low level of FVIII, peak thrombin was unaffected, and only a small decrease in the AUC was observed. Even at a FVIII concentration of 0.005 IU/ml the AUC was only slightly lower than that of normal plasma, 6287 and 6540 iu.sec respectively. At concentrations of 1 ($T_{1/2\ max}$ 64 sec) and 0.125 IU/ml ($T_{1/2max}$ 87 sec) thrombin was generated more rapidly than normal plasma ($T_{1/2max}$ 118 sec), and a concentration of 0.03 IU/ml ($T_{1/2max}$ 119 sec) had a similar thrombin generation profile to that of normal plasma.

EXAMPLE 3

Comparison of FVIII Concentrates

When various different FVIII concentrates were added to the FVIII deficient plasma at the same FVIII:C concentration, thrombin generation curves were obtained that were similar to concentrate HP(Mo-Ab)2 (FIG. 1B, Table 2). All concentrates at 1 IU/ml produced thrombin more rapidly, and in greater quantity, than normal plasma. The $T_{1/2\ max}$ of rFVIII BDD (48 sec) was shorter than that of the other concentrates (range 54-64 sec); this difference was statistically significant, p<0.05.

EXAMPLE 4

Severe Haemophilic Plasma

Figure 2:
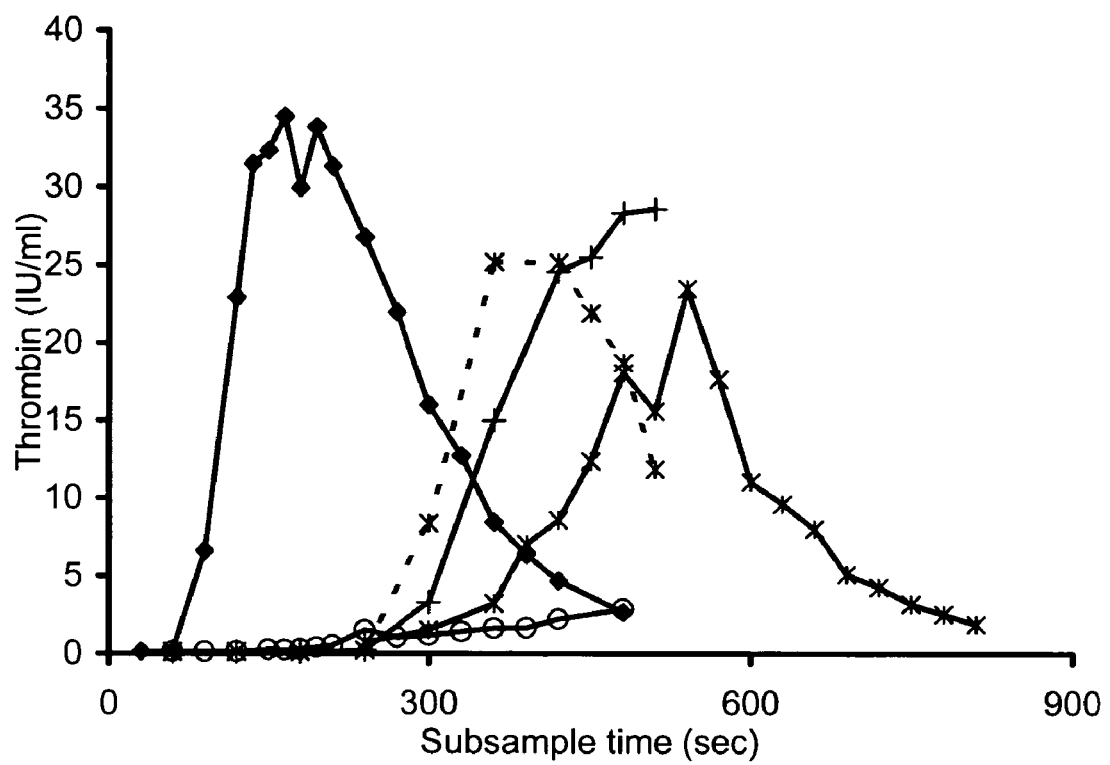

Plasma from two patients with severe haemophilia A generated a surprising amount of thrombin (FIG. 2, Table 3), with AUC 65 and 69% of normal plasma despite having levels of less than 0.01 IU/ml. However, the onset of thrombin generation was considerably delayed, $T_{1/2max}$ (426 and 318 seconds) for both patients. Overnight incubation with a FVIII antibody resulted in complete abolition of thrombin generation, peak thrombin from 22 IU/ml to 0.2 IU/ml (Table 3), indicating that the thrombin generated by these haemophilic plasmas can be attributed to low levels of FVIII. Another sample of plasma was obtained from patient HP1 at 61 hours post-infusion (original sample 37 hours post-infusion), this sample produced minimal thrombin generation (AUC 5% of normal plasma). This suggests that the thrombin generation test under these conditions is sensitive to levels below the limit of detection by 1-stage assay i.e. <0.01 IU/ml.

EXAMPLE 5

FIXa Concentration

The concentration of FIXa was attenuated (FIG. 3A) in order to check the influence of FIXa on thrombin generation at very low FVIII concentrations. Decreasing FIXa concentration from 14 nM progressively prolonged the lag-time of normal plasma ($T_{1/2max}$ 114 sec at 14 nM to 226 sec at 0.2 nM) but caused no change in peak height or AUC (at 0.2 nM AUC 98% of 14 nM). In contrast to results with 14 nM, at a FIXa concentration of 0.2 nM in haemophilic plasma virtually no thrombin was generated. The thrombin generation test is therefore sensitive to the low amounts of FVIII but is dependent also on the concentration of FIXa. Experiments (data not shown) have indicated that the normal and haemophilic plasma produced similar amounts of thrombin by glass contact activation as the high FIXa concentration.

EXAMPLE 6

Dose-Response of FVIII at Low FIXa Concentration

Figure 3:
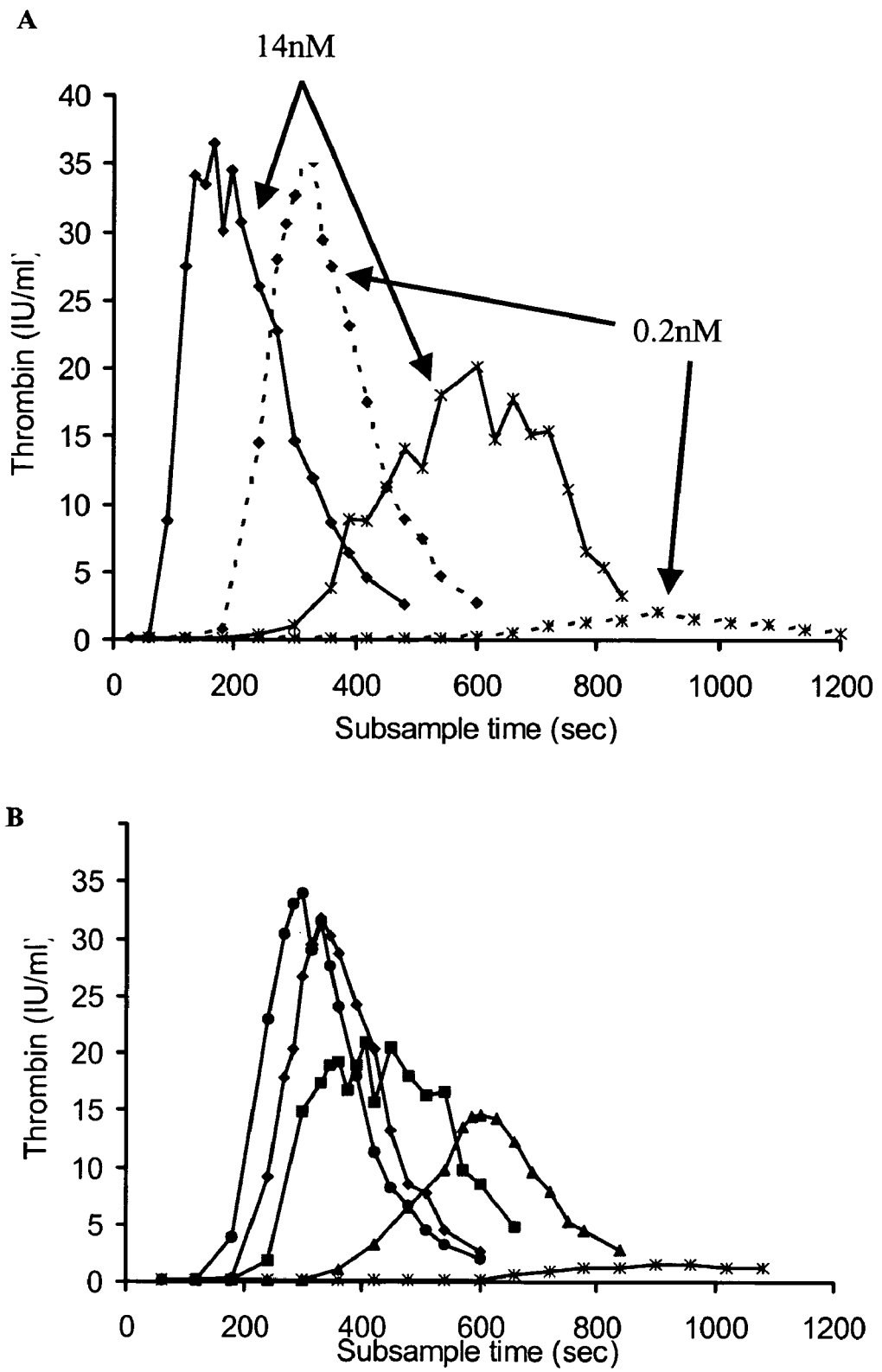

The same concentrate HP(Mo-Ab)2 was used again to asses the dose-response at low Fixa levels. The concentrate was diluted into haemophilic plasma and a low FIXa (0.2 nM) concentration was used to activate the plasma (FIG. 3B). As FVIII concentration decreased, AUC and peak height also decreased, and the lag time increased (as was observed previously). In contrast to the high FIXa concentration peak height and AUC remained abnormal, and were only normalised by much higher FVIII concentrations. The effect on thrombin generation with increasing FVIII was more marked at lower FIXa concentrations.

Discussion

The more rapid thrombin generation seen with the chemically depleted plasma was shown to be an artefact of the particular deficient plasma used. The same phenomenon was not observed with immuno-depleted and haemophilic plasmas, but the total amount of thrombin generated at low levels was still high, and was shown to be due to the high FIXa concentration used.

With a high FIXa concentration the thrombin generation test (TGT) was found to be very sensitive to low levels of FVIII. A large amount of thrombin was generated when FVIII levels were less than 0.01 IU/ml by both an artificial situation with FVIII concentrate added to FVIII deficient plasma, and in two severe haemophilic plasmas. Early work on the TGT found that only very small amounts of thrombin could be detected in haemophilic plasma, however only small additions of normal plasma were required to improve the thrombin generation. Macfarlane and Biggs (A thrombin generation test: the application in haemophilia and thrombocytopenia. J Clin Pathol 1953; 6: 3-8) in their plasma studies showed that an addition of 0.5% normal blood to haemophilic blood caused a detectable thrombin generation, however, it was much prolonged and was only one third of the average peak height of the normal samples. Pitney and Dacie found that addition of 1% normal plasma improved thrombin generation, but that 20% or more was required to bring the thrombin generation within the normal limits (Pitney W R and Dacie J V. A simple method for studying the generation of thrombin in recalcified plasma. J Clin Pathol 1953; 6: 9-14). The use of a FVIII antibody on a haemophilic sample (HP1) demonstrated that thrombin generated below 0.01 IU/ml was due to FVIII (table 3). A repeat sample from this patient was taken after a longer duration post-infusion and generated hardly any thrombin, suggesting that the thrombin generated from the original sample was due to residual FVIII from the infusion. Plasma from another patient (HP2) was collected at 72 hours post-infusion and the thrombin generated is unlikely to be due to the infusion, but probably due to endogenous FVIII. In a recent study the aPTT clot waveform analysis has shown detectable FVIII in some severe haemophilic patients with levels measured between 0.002 and 0.01 IU/ml (Shima M, Matsumoto T, Fukuda K, Kubota Y, Tanaka I, Nishiya K, Giles A R, and Yoshioka A. The utility of activated partial thromboplastin time (aPTT) clot waveform analysis in the investigation of hemophilia A patients with very low levels of factor VIII activity (FVIII:C). Thromb Haemost 2002; 87: 436-441). As this low level of FVIII can be measured it has implications for the frequency of prophylaxis. We have demonstrated considerable thrombin generation at less than 0.01 IU/ml, and there is some evidence to suggest that with trough levels of less than 0.01 IU/ml joint bleeds are still rare (Petrini P. What factors should influence the dosage and interval of prophylactic treatment in patients with severe haemophilia A and B? Haemophilia 2001; 7: 99-102). Although it is generally accepted that prophylaxis should be maintained above this level, it has not been proven that this leads to an improved clinical outcome (van den Berg H M, Fischer K, Mauser-Bunschoten E P, Beek F J, Roosendaal G, van der Bom J G, and Nieuwenhuis H K. Long-term outcome of individualized prophylactic treatment of children with severe haemophilia. Br J Haematol 2001; 112: 561-565).

The sensitivity of the TGT to low levels of FVIII may be explained by the amount of FIXa used in the assay to initiate coagulation. It was found that the FIXa concentration was important in the ability of low concentrations of FVIII to generate thrombin, but this effect was minimised as levels of FVIII normalised. The high FIXa concentration was originally chosen as it produced the same thrombin generation profile as intrinsic glass contact activation. Josso et al (Josso F, and Prou-Wartelle O. Interaction of tissue factor and factor VII at the earliest phase of coagulation. Thromb Diath Haemorrh Suppl 1965; 17: 35-44) demonstrated that tissue factor (TF) and FVII were required to bypass the need for contact activation in vitro. It was later shown that TF, FVII and calcium activate FIX (Østerud B, and Rapaport S I. Activation of factor IX by the reaction product of tissue factor and factor VII. Additional pathway for initiating blood coagulation. Proc Natl Acad Sci USA 1977; 74: 5260-5264). This has also been shown to occur at low TF concentrations, which explains the role of the anti-haemophilic factors in thrombin generation (Bauer K A. Activation of the factor VII-tissue factor pathway. Thromb Haemost 1997; 78: 108-111; Keularts I M, Zivelin A, Seligsohn U, Hemker H C, and Beguin S. The role of factor XI in thrombin generation induced by low concentrations of tissue factor. Thromb Haemost 2001; 85: 1060-1065). In addition, at low concentrations of TF, less than 1% of total plasma FIX is activated, giving a plasma FIXa concentration of 0.9 nM (Lawson J H, Kalafatis M, Stram S, and Mann K G. A model for the tissue factor pathway to thrombin. J Biol Chem 1994; 269: 23357-23366). The low FIXa concentration of 0.2 nM that has been used in these experiments is therefore lower than this but could be considered to be a physiological concentration present during initiation of the coagulation cascade. The higher FIXa concentration of 14 nM used to trigger thrombin generation, although similar to contact activation, would perhaps appear to be higher than physiological, although local concentrations of FIXa following injury may be higher than 0.9 nM. Other work has used FIXa concentrations of 0.1 nM to 1.5 nM in the TGT (Hoffman M, Monroe D M, Oliver J A, and Roberts H R. Factor IXa and Xa play distinct roles in tissue factor-dependent initiation of coagulation. Blood 1995; 86: 17941-1801; Jesty J. Interactions of feedback control and product inhibition in the activation of factor X by factors IXa and VIII. Haemostasis 1991; 21: 208-218; Kumar R, Beguin S, and Hemker H C. The influence of fibrinogen and fibrin on thrombin generation-evidence for feedback activation of the clotting system by clot bound thrombin. Thromb Haemost 1994; 72: 713-721; Sekiya F, Yoshida M, Yamashita T, and Morita T. Magnesium (II) is a crucial constituent of the blood coagulation cascade. Potentiation of coagulant activities of FIX by $Mg^{2+}$ ions J Biol Chem 1996; 271: 8541-8544). Without wishing to be bound by any particular theory, it may be that at high FIXa concentrations when assaying low concentrations of FVIII the FIXa protects what little FVIIIa is produced by the haemophilic plasma from degrading (Lenting P J, van Mourik J A, Mertens K. The life cycle of coagulation factor VIII in view of its structure and function. Blood 1998; 92: 3983-3996), and at much higher FIXa concentrations FIXa can enhance FVIII:C activity (Rick M E. Activation of factor VIII by factor IXa. Blood 1982; 60: 744-751).

The invention will now be further described by the following numbered paragraphs:

1. Use of FIXa and FVIII in the preparation of a composition for the treatment of haemophilia A or haemophilia B in a subject which does not present with anti-FVIII antibodies.
2. A composition comprising FIXa and a composition comprising FVIII for simultaneous, simultaneous separate or sequential use in the treatment of haemophilia A or haemophilia B in a subject which does not present with anti-FVIII antibodies.
3. A composition comprising FIXa according to paragraph 1 or claim 2, which further comprises phospholipid.
4. Use of FIXa in the manufacture of a composition comprising FVIII for the treatment of haemophilia A or haemophilia B, wherein the presence of Fixa allows the concentration of FVIII in the composition to be reduced in comparison to a composition which does not comprise FIXa.
5. Use according to paragraph 4, wherein the composition is administered to a subject which does not present with anti-FVIII antibodies.
6. Use according to paragraph 4 or paragraph 5, wherein the FVIII and FIXa reagents are produced using recombinant DNA technology.
7. Use according to any one of paragraphs 4 to 6, wherein the composition further comprises phospholipid.
8. Use according to any one of paragraphs 4 to 7, wherein the composition is formulated to provide FVIII to a subject at a dosage of between 2 and 10 IU/kg.
9. A method for treating a subject suffering from haemophilia A or haemophilia B, comprising administering to a subject in need thereof a composition comprising FIXa and FVIII, wherein said subject does not present with anti-FVIII antibodies.
10. A method for treating a subject suffering from haemophilia A or haemophilia B, comprising administering to a subject in need thereof a composition comprising FIXa and FVIII, wherein said composition comprises FVIII in an amount lower than that required for treatment of said subject with a composition lacking FIXa.
11. A method according to paragraph 9 or paragraph 10, wherein said composition further comprises phospholipid.
12. A method according to any one of paragraphs 9 to 11, wherein the composition comprises recombinant FIXa and recombinant FVIII.
13. A method according to any one of paragraphs 9 to 12, wherein the composition is formulated to provide FVIII to a subject at a dosage of between 2 and 10 IU/kg.
14. A method for potentiating FVIII comprising the step of mixing together Factor FVIII and FIXa into a composition.
15. A method according to paragraph 14, wherein said composition further comprises phospholipid.
16. A method according to paragraph 14 or paragraph 15, wherein the composition comprises recombinant FIXa and recombinant FVIII.
17. A method for reducing the immunogenicity of FVIII in a composition comprising FVIII in a subject, comprising administering FVIII together with FIXa to the subject.
18. Use of FIXa and FVIII in the preparation of a composition for the treatment of haemophilia, wherein the FVIII in said composition has reduced immunogenicity as a result of the presence of FIXa.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in biology or related fields are intended to be within the scope of the following claims.

TABLE 1

Properties of FVIII concentrates

| Concentrate | Abbreviation | NIBSC code | Fractionation | vWF |
|---|---|---|---|---|
| B domain deleted | rFVIII BDD | 99/694 | Recombinant | None |
| Full length recombinant 1 | rFVIII FL1 | 96/598 | Recombinant, ion exchange and immuno affinity chromatography | None |
| Full length recombinant 2 | rFVIII FL2 | 96/590 | Recombinant, ion exchange and immuno affinity chromatography | None |
| High purity monoclonal antibody purified 1 | HP(Mo-Ab)1 | 96/574 | Monoclonal antibody affinity chromatography | No functional vWF |
| High purity monoclonal antibody purified 2 | HP(Mo-Ab)2 | 95/640 | Monoclonal antibody affinity chromatography | No functional vWF |
| High purity ion-exchange | HP(Ion-Ex) | 96/600 | Ion exchange chromatography | Contains vWf |
| Intermediate purity | IP | 96/576 | Heparin/glycine precipitate | Contains vWF |

TABLE 2

Thrombin generation of FVIII concentrates at 1 IU/ml * = P < 0.05. Area under the curve (AUC), time taken to reach half maximal peak height ($T_{1/2max}$), $n \geq 3$.

| | AUC | SD | $T_{1/2max}$ | SD | Peak | SD |
|---|---|---|---|---|---|---|
| rFVIII BDD | 7888 | 758 | 48* | 8 | 40 | 2 |
| rFVIII FL1 | 7514 | 649 | 57 | 8 | 39 | 2 |
| rFVIII FL2 | 7519 | 1496 | 64 | 6 | 38 | 3 |
| HP (Mo—Ab)1 | 7789 | 997 | 63 | 8 | 40 | 3 |
| HP (Mo—Ab)2 | 7195 | 811 | 64 | 15 | 38 | 3 |
| HP (Ion-ex) | 7700 | 799 | 54 | 4 | 41 | 2 |
| IP | 7246 | 815 | 64 | 9 | 40 | 2 |
| Normal plasma | 6174 | 735 | 118 | 9 | 38 | 3 |

TABLE 3

Results of thrombin generation by FVIII deficient plasma. All deficient plasmas contain FVIII <0.01 IU/ml. Haemophilic plasma (HP), $n \geq 3$.

| | AUC | SD | $T_{1/2max}$ | SD | Peak | SD |
|---|---|---|---|---|---|---|
| Normal Plasma | 6934 | 749 | 108 | 16 | 39 | 4 |
| HP1 (37 hrs post-infusion) | 4532 | 753 | 426 | 65 | 22 | 5 |
| HP1 (61 hrs post-infusion) | 331 | 253 | — | — | 1 | 2 |
| HP2 (72 hrs post-infusion) | 4765 | 339 | 318 | 26 | 31 | 6 |
| Commercial HP | 4561 | 1493 | 365 | 54 | 32 | 3 |
| Artificial FVIII def | 587 | 136 | 288 | 12 | 4 | 1 |
| HP1 + FVIII Ab | 146 | 38 | — | — | 0.2 | 0.1 |

The invention claimed is:

1. A method of treating Haemophilia A or Haemophilia B, comprising administering by injection to a patient in need thereof an effective amount of a sterile pharmaceutical composition consisting essentially of coagulation Factors VIII and IXa, wherein the coagulation Factor IXa reduces the concentration of coagulation Factor VIII in the composition in comparison to a composition which does not comprise coagulation Factor IXa, and wherein said patient does not present with anti-coagulation Factor VIII antibodies.

2. The method of claim 1, wherein the coagulation Factor VIII is a von Willebrand Factor (vWF) B domain deleted rFVIII (recombinant Factor VIII).

3. The method of claim 1, wherein the sterile pharmaceutical composition further comprises phospholipid.

4. The method of claim 1, wherein the sterile pharmaceutical composition is formulated to provide coagulation Factor VIII to said patient at a dosage of between 2 and 10 IU/kg.

* * * * *